US00PP29831P2

(12) United States Plant Patent
Wood

(10) Patent No.: US PP29,831 P2
(45) Date of Patent: Nov. 13, 2018

(54) ***SYRINGA* PLANT NAMED 'SMNJRPU'**

(50) Latin Name: ***Syringa* hybrid**
Varietal Denomination: SMNJRPU

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,482

(22) Filed: Nov. 20, 2017

(51) Int. Cl.
*A01H 5/02* (2018.01)

(52) U.S. Cl.
USPC ..... Plt./248
CPC ..... *A01H 5/02* (2013.01)

(58) Field of Classification Search
USPC ..... Plt./248
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Syringa* cultivar named 'SMNJRPU' is disclosed, characterized by sweet scented, purple flowers. Plants are dwarf and compact with re-blooming characteristics. The new variety is a *Syringa* normally produced as an outdoor garden or container plant.

2 Drawing Sheets

Latin name of the genus and species: *Syringa* hybrid.
Variety denomination: 'SMNJRPU'.

BACKGROUND OF THE INVENTION

The present invention comprises a new and distinct variety of *Syringa*, hereinafter referred to by the cultivar name 'SMNJRPU'. This new *Syringa* was developed through a breeding program in Grand Haven, Mich. The objective of the breeding program was to develop new *Syringa* varieties with reblooming flowers, in new flower colors. 'SMNJRPU' is an internal, advanced selection from an in-house breeding program. The seed parent is an unnamed, unpatented proprietary breeding line. The pollen parent is unidentified as the new variety was produced through an open pollination breeding program. The open pollination resulting in the new variety was made in 2010. Selection of the new variety was made during 2013.

The first asexual propagation of 'SMNJRPU' was carried out during 2013 by softwood cuttings at a commercial nursery in Grand Haven, Mich. 'SMNJRPU' has been found to retain its distinctive characteristics through successive asexual propagations. Multiple generations have been asexually propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Dwarf, compact plant habit.
2. Good floral fragrance.
3. Reblooming habit.
4. Purple flowers.

COMPARISON WITH THE PARENT VARIETIES

'SMNJRPU' is similar to the seed parent *Syringa* in most horticultural characteristics. 'SMNJRPU', however, differs in the following:

1. New cultivar has purple flowers, while the seed parent has pink flowers.

COMMERCIAL COMPARISON

'SMNJRPU' is similar to the commercial variety *Syringa* 'Penda', U.S. Plant Pat. No. 24,252, in most horticultural characteristics. 'SMNJRPU', however, differs in the following:

1. Plants of the new variety are more compact and dwarf, this comparator is a larger plant.
2. Plants of the new variety have darker purple flowers, comparator has lighter purple flowers.

DESCRIPTION OF THE PHOTOGRAPHS

This new *Syringa* is illustrated by the accompanying photographs which show the plant's form, foliage and inflorescences. The colors shown are as true as can be reasonably obtained by conventional photographic procedures. Plants were grown in Grand Haven, Mich.

Figure 1:
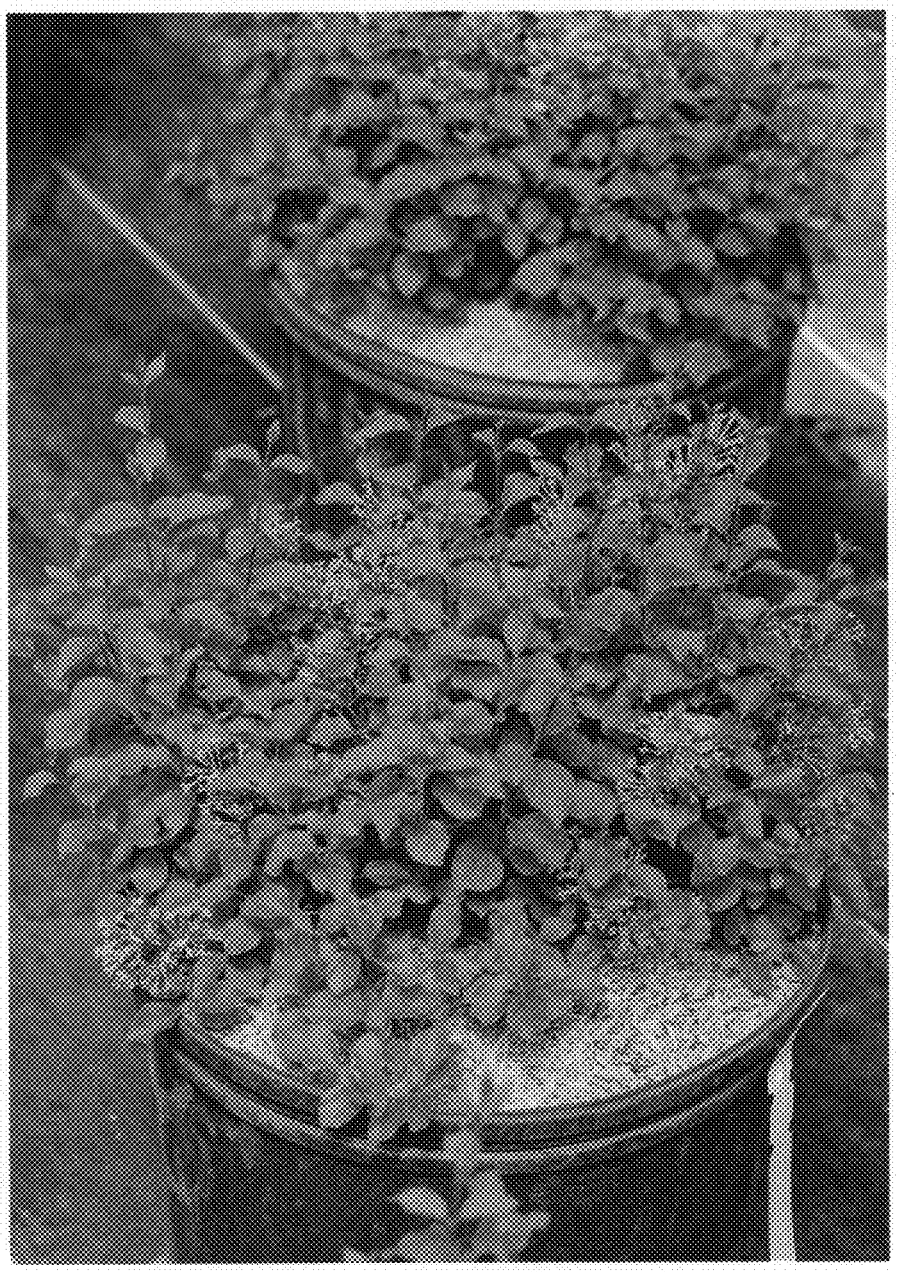

FIG. 1. Shows a flowering plant of 'SMNJRPU' in a 3 gallon pot at approximately 1.5 years old during Summer.

Figure 2:
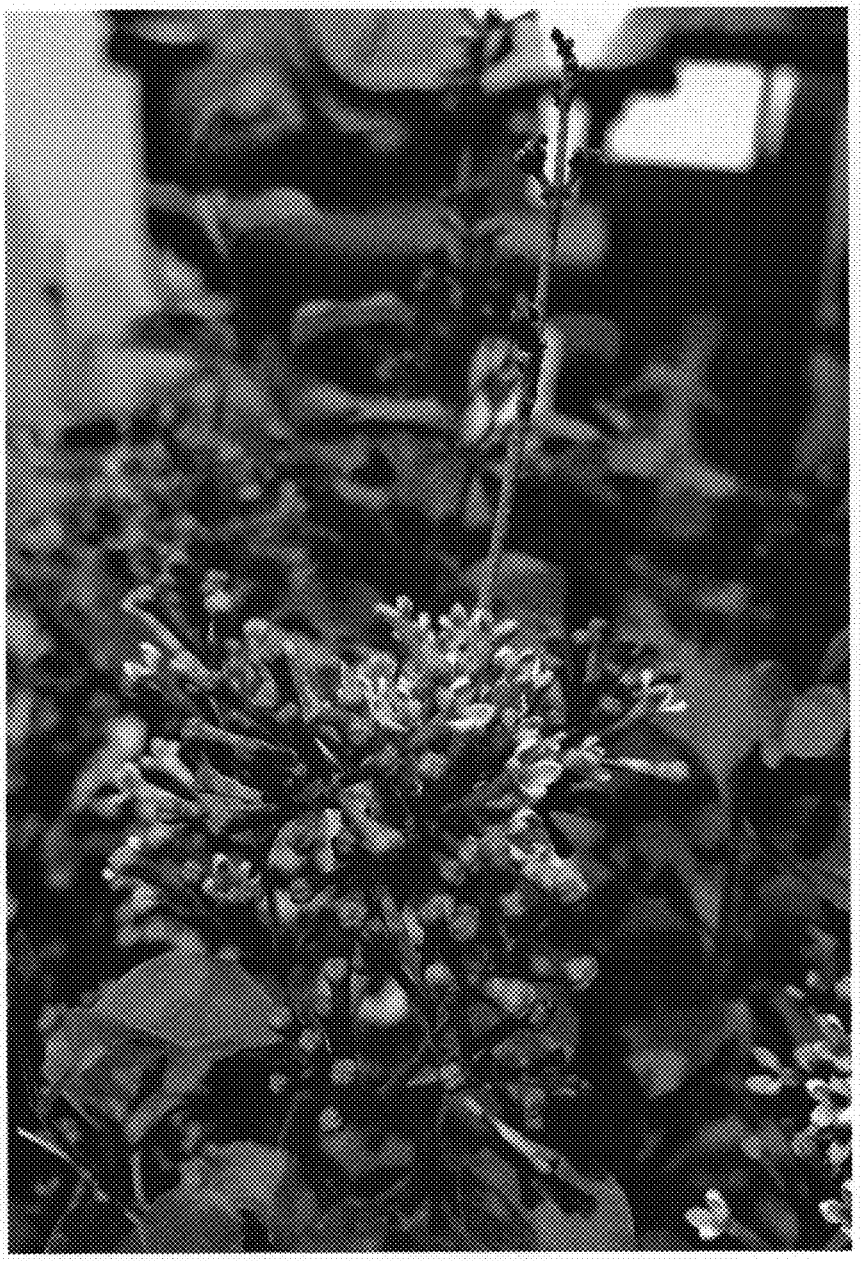

FIG. 2. Shows a close-up view of the inflorescence.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNJRPU' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Syringa* hybrid 'SMNJRPU'.
Propagation:
Typical method: Softwood cuttings.
Time to initiate rooting: About 20 days at approximately 18° C. to 27° C.
Time to produce a rooted young plant: About 3 months at approximately 18° C. to 27° C.
Root description: Dense, free branching, thin, fibrous. Colored white, not accurately measured with an R.H.S. chart.
Plant description:
*Age of plant described.*—About 2 years in a 3 gallon container.
*Type of plant.*—Perennial shrub.
*Growth habit.*—Rounded.
*Height.*—51 cm in a 3 gallon container.
*Width.*—51 cm in a 3 gallon container.
*Growth rate.*—Good.
*Typical commercial container sizes.*—1, 2, and 3 gallon.
Branches:
*Branching habit.*—Freely branching.
*Lateral branch quantity.*—8.
*Lateral branch length.*—33 cm.
*Lateral branch diameter.*—3 mm.
*Branch angle.*—0-45 degrees.
*Branch strength.*—Moderate.
*Branch color.*—Grey-Brown 199C.
*Internode length.*—3.5 cm.
Foliage:
Leaves:
*Arrangement.*—Opposite.
*Length.*—Avg. 2.4 cm.
*Width.*—Avg. 1.9 cm.
*Shape.*—Ovate.
*Apex.*—Acute.
*Base.*—Obtuse.
*Margin.*—Entire.
*Texture upper surface.*—Slightly rough.
*Texture lower surface.*—Slightly rough.
*Color.*—Immature: Upper: Mostly Green 137 C with greyed purple 183 C around the edges. Lower: Partly Green 137 C with greyed purple 183 C near the bottom. Mature: Upper: Green 137B. Lower: Yellow Green 144A. Fall foliage color: Upper: Near Yellow-Orange 14B and 14C, both colors present. Lower: Near Yellow 11C.
*Petiole.*—Length: 4 mm. Width: Average 1 mm. Texture: Slightly pubescent, more pubescent on bottom. Color: New growth upper surface: Greyed-Red 180C. New growth lower surface: Greyed-Red 182D.
Inflorescence:
*Description.*—Panicle.
*Flowering season.*—Spring to Mid-Summer.
*Fragrance.*—Light and sweet.
*Number of flowers per inflorescence.*—50 to 100.
*Inflorescence height.*—6.0 cm.
*Inflorescence diameter.*—6-8 cm.
Flowers:
*Flower diameter.*—5 mm.
*Flower depth.*—1.2 cm.
*Flower throat diameter.*—2 mm.
*Flower tube diameter (base).*—1 mm.
*Flower tube length.*—9 mm.
*Flower angle.*—Upward or outward.
*Persistent or self-cleaning.*—Self-Cleaning.
*Flower bud.*—Length: 1 cm. Diameter: 2 mm. Shape: Obovate. Color: New: Purple 77A. Close to opening: Purple 77C.
*Petals.*—Number: 4. Arrangement: Rotate. Length: 3 mm. Width: 2 mm. Shape: Ovate. Apex: Acute, slightly cupped. Base: Fused. Margin: Entire Texture: Upper side: Smooth. Lower side: Smooth. Color: When opening, upper side: About 50/50 Purple 77C and 77B. When opening, under side: Purple 77C. Fully opened, upper side: About 50/50 Purple 77C and 77B. Fully opened, under side: Purple 77C. Flower tube: 50/50 Purple 77A and 77B. Flower throat: Purple 77A.
*Sepals.*—Extremely minute (less than 1 mm by 1 mm in size) and inconspicuous.
*Peduncle.*—Length: 3 cm. Width: 1 mm. Color: Greyed-Purple 183A. Texture: Smooth, pubescent. Angle: Upright/outward. Strength: Moderate.
*Pedicels.*—Length: 3-5 mm. Diameter: 1 mm. Texture: Smooth, pubescent. Color: Greyed-Purple 183A. Strength: Good. Angle: Upright/outward.
Reproductive organs:
*Gynoecium.*—Pistil number: 1. Pistil length: 3 mm. Stigma shape: Oblong to rounded. Stigma color: Close to White 155A. Style length: about 2 mm. Style color: Close to White 155A.
*Androecium.*—Stamen number: 2. Filament length: 1.5 mm. Filament color: Grey 201A. Anther shape: Oblong. Anther size: 2 mm. Anther color: Grey 201A. Amount of pollen: Some. Pollen color: Green-Yellow 1A.

OTHER CHARACTERISTICS

Fruit: Not observed to date.
Disease and insect resistance: No significant disease or pest resistance nor susceptibility have been observed.
Temperature range: Observed to tolerate temperatures between −33° C. and 36° C.

What is claimed is:

1. A new and distinct *Syringa* plant named 'SMNJRPU' as illustrated and described herein.

* * * * *